US011934938B2

United States Patent
Hara et al.

(10) Patent No.: US 11,934,938 B2
(45) Date of Patent: *Mar. 19, 2024

(54) NEURAL NETWORK FOR CHEMICAL COMPOUNDS

(71) Applicant: INTERNATIONAL BUSINESS MACHINES CORPORATION, Armonk, NY (US)

(72) Inventors: Satoshi Hara, Tokyo (JP); Gakuto Kurata, Tokyo (JP); Shigeru Nakagawa, Tokyo (JP); Seiji Takeda, Tokyo (JP)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 577 days.

This patent is subject to a terminal disclaimer.

(21) Appl. No.: 17/132,631

(22) Filed: Dec. 23, 2020

(65) Prior Publication Data

US 2021/0110240 A1 Apr. 15, 2021

Related U.S. Application Data (63) Continuation of application No. 15/202,211, filed on Jul. 5, 2016, now Pat. No. 10,915,808.

(51) Int. Cl.
*G06N 3/04* (2023.01)
*G06N 3/045* (2023.01)
(Continued)

(52) U.S. Cl.
CPC .............. *G06N 3/045* (2023.01); *G16C 20/70* (2019.02); *G16C 99/00* (2019.02)

(58) Field of Classification Search
CPC ......... G06N 3/045; G16C 20/70; G16C 99/00
See application file for complete search history.

(56) References Cited

U.S. PATENT DOCUMENTS 5,438,644 A * 8/1995 Fu .......................... G06N 3/042
706/45
6,625,585 B1 9/2003 MacCuish et al.
(Continued)

FOREIGN PATENT DOCUMENTS

WO WO1999035599 * 7/1999 ............. G06F 17/50
WO WO0063421 10/2000

OTHER PUBLICATIONS

Daylight Chemical Information Systems, Inc., "Daylight Theory: SMARTS—A Language for Describing Molecular Patterns," Daylight Chemical Information Systems, Inc. Retrieved Jun. 2016. (pp. 1-8). Available at: http://www.daylight.com/dayhtml/doc/theory/theory.smarts.html.
(Continued)

*Primary Examiner* — Omar F Fernandez Rivas
*Assistant Examiner* — Tri T Nguyen
(74) *Attorney, Agent, or Firm* — Tutunjian & Bitetto, P.C.; Robert Richard Aragona (57) ABSTRACT

A computer implemented method for training a neural network to capture a structural feature specific to a set of chemical compounds is disclosed. In the method, the computer system reads an expression describing a structure of the chemical compound for each chemical compound in the set and enumerates one or more combinations of a position and a type of a structural element appearing in the expression for each chemical compound in the set. The computer system also generates training data based on the one or more enumerated combinations for each chemical compound in the set. The training data includes one or more values with a length, each of which indicates whether or not a corresponding type of the structural element appears at a corresponding position for each combination. Furthermore, the
(Continued)

computer system trains the neural network based on the training data for the set of the chemical compounds.

20 Claims, 5 Drawing Sheets

(51) Int. Cl.
*G16C 20/70* (2019.01)
*G16C 99/00* (2019.01)

(56) References Cited

U.S. PATENT DOCUMENTS

| | | | | |
|---|---|---|---|---|
| 6,904,423 | B1* | 6/2005 | Nicolaou | G06N 5/02 |
| | | | | 702/22 |
| 8,364,408 | B2* | 1/2013 | Srinivasa | G16B 30/10 |
| | | | | 703/11 |
| 8,515,684 | B2 | 8/2013 | Boyer et al. | |
| 2003/0048341 | A1* | 3/2003 | Mutz | B41J 2/04 |
| | | | | 506/40 |
| 2003/0130799 | A1* | 7/2003 | Pidgeon | G16B 15/30 |
| | | | | 703/11 |
| 2003/0229456 | A1* | 12/2003 | Beger | G01N 33/48 |
| | | | | 702/27 |
| 2004/0009536 | A1* | 1/2004 | Grass | G16C 20/30 |
| | | | | 703/11 |
| 2004/0199334 | A1* | 10/2004 | Kovesdi | G16C 20/30 |
| | | | | 703/11 |
| 2008/0133434 | A1 | 6/2008 | Asar et al. | |
| 2015/0193462 | A1* | 7/2015 | Kataoka | G06F 16/90344 |
| | | | | 707/693 |
| 2017/0177993 | A1* | 6/2017 | Draelos | G06N 3/045 |
| 2018/0121800 | A1* | 5/2018 | Kanda | G06N 3/04 |

OTHER PUBLICATIONS

Duvenaud, D. et al., "Convolutional Networks on Graphs for Learning Molecular Fingerprints," arXiv 1509.09292v2 [cs.LG], Nov. 2015. (pp. 1-9). Available at: http://arxiv.org/pdf/1509.09292.pdf.

JRC Computational Toxicology Group, "How to Create SD/SDF Files From Smiles Using Freely Available Software Tools," JRC Computational Toxicology Group, Dec. 2009. (pp. 1-2).

Weininger, D. et al., "SMILES. 2. Algorithm for Generation of Unique SMILES Notation," J. Chem. Inf. Comput. Sci., vol. 29, No. 2, May 1989. (pp. 97-101).

List of IBM Patents or Patent Applications Treated as Related dated Dec. 23, 2020, 2 pages.

* cited by examiner

C=CCC#N

FIG. 3B

| TYPE\POSITION | 1 | 2 | 3 | 4 | 5 | 6 | 7 | 8 | 9 | 10 |
|---|---|---|---|---|---|---|---|---|---|---|
| C | 1 |  | 1 | 1 | 1 |  |  |  |  |  |
| N |  |  |  |  |  |  | 1 |  |  |  |
| = |  | 1 |  |  |  |  |  |  |  |  |
| # |  |  |  |  |  | 1 |  |  |  |  |

| TYPE\POSITION | 1 | 2 | 3 | 4 | 5 | 6 | 7 | 8 | 9 | 10 |
|---|---|---|---|---|---|---|---|---|---|---|
| C |  | →  |  | 1 | 1 | 1 |  |  |  |  |
| N |  |  |  |  |  |  |  | 1 |  |  |
| = |  |  | 1 |  |  |  |  |  |  |  |
| # |  |  |  |  |  |  | 1 |  |  |  |

FIG. 4A

| TYPE\POSITION | 1 | 2 | 3 | 4 | 5 | 6 | 7 | 8 | 9 | 10 |
|---|---|---|---|---|---|---|---|---|---|---|
| C |  | •————→ |  |  | 1 | 1 | 1 |  |  |  |
| N |  |  |  |  |  |  |  |  |  | 1 |
| = |  |  |  |  | 1 |  |  |  |  |  |
| # |  |  |  |  |  |  |  |  | 1 |  |

FIG. 4B

| TYPE\POSITION | 1 | 2 | 3 | 4 | 5 | 6 | 7 | 8 | 9 | 10 |
|---|---|---|---|---|---|---|---|---|---|---|
| C | 1 |  | 1 | • | 1 | • | • | 1 |  |  |
| N |  |  |  | | | | |  |  | 1 |
| = |  | 1 |  | | | | |  |  |  |
| # |  |  |  | • |  | • | • |  | 1 |  |

FIG. 4C

| TYPE\POSITION | 1 | 2 | 3 | 4 | 5 | 6 | 7 | 8 | 9 | 10 |
|---|---|---|---|---|---|---|---|---|---|---|
| C | 1 |  | 1 | • | • | • | 1 | 1 |  |  |
| N |  |  |  | | | |  |  |  | 1 |
| = |  | 1 |  | | | |  |  |  |  |
| # |  |  |  | • | • | • |  |  | 1 |  |

NEURAL NETWORK FOR CHEMICAL COMPOUNDS

BACKGROUND

The present invention, generally, relates to machine learning techniques for neural networks in chemistry, more particularly, to training of a neural network to capture a structural feature specific to a set of chemical compounds.

Neural networks have been widely used in various fields including image classification, automatic speech recognition, natural language processing, etc. Recently, the neural networks have been applied to chemistry in order to classify chemical compounds.

There are known various SDFs (Structured Data Formats) for handling the chemical structures of the chemical compounds on a computer system, which may include SMILES (Simplified Molecular Input Line Entry System), SMARTS (SMiles ARbitrary Target Specification), etc. Since the number of elements such as atoms and bonds, and the number of types of the elements varies depending on the specific chemical structure of the chemical compounds, an expression with a variable length may be assigned to each specific chemical compound.

To handle the expression with the variable length in the neural network, Convolutional Neural Networks (CNNs) combined with pooling operation and Recurrent Neural Networks (RNNs), which can accept the expression with variable length as it is, has been employed. The CNN and RNN may be effective if it is specialized for classification. However, there is still needed an improved neural network that is suitable for handling chemical compounds.

SUMMARY

According to an embodiment of the present invention, there is provided a computer implemented method for training a neural network to capture a structural feature specific to a set of chemical compounds. The method includes reading an expression that describes a structure of the chemical compound, for each chemical compound in the set. The method also includes enumerating one or more combinations of a position and a type of a structural element appeared in the expression, for each chemical compound in the set. The method further includes generating training data based on the one or more enumerated combinations for each chemical compound in the set. The training data includes one or more values with a size, each of which indicates whether or not a corresponding type of the structural element does appear at a corresponding position for each combination. Furthermore, the method includes training the neural network based on the training data for the set of the chemical compounds.

Computer systems and computer program products relating to one or more aspects of the present invention are also described and claimed herein.

Additional features and advantages are realized through the techniques of the present invention. Other embodiments and aspects of the invention are described in detail herein and are considered a part of the claimed invention.

BRIEF DESCRIPTION OF THE DRAWINGS

The subject matter, which is regarded as the invention, is particularly pointed out and distinctly claimed in the claims at the conclusion of the specification. The forgoing and other features and advantages of the invention are apparent from the following detailed description taken in conjunction with the accompanying drawings in which:

DETAILED DESCRIPTION

Now, the present invention will be described using particular embodiments, and the embodiments described hereafter are understood to be only referred as examples and are not intended to limit the scope of the present invention.

One or more embodiments according to the present invention are directed to a computer implemented method, computer system and computer program product for training a neural network to capture a structural feature specific to a set of chemical compounds.

Now, referring to the series of FIGS. 1-4, it will be described a computer system and method for extracting a structural feature specific to a set of chemical compounds by way of a neural network, according to an exemplary embodiment of the present invention. In the exemplary embodiment of the present invention, information related to the specific structural feature would be extracted by analyzing the neural network that is trained by a novel training technique so as to enable it to capture the structural feature specific to the set of the chemical compounds.

Figure 1:
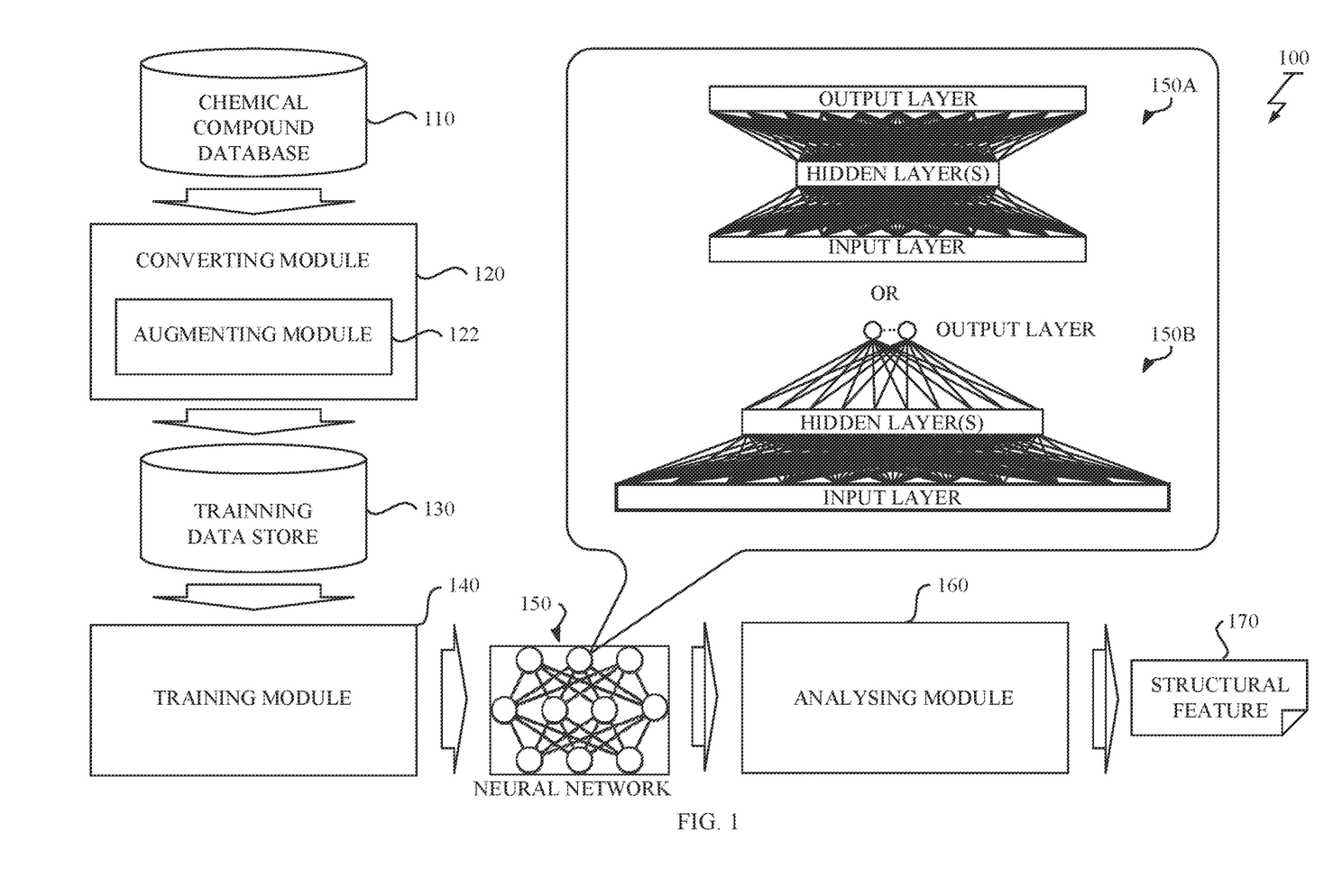
FIG. 1 illustrates a block diagram of a chemical structure analyzing system according to an exemplary embodiment of the present invention.

FIG. 1 illustrates a block diagram of a chemical structure analyzing system 100 according to the exemplary embodiment of the present invention. As shown in FIG. 1, the chemical structure analyzing system 100 may include a chemical compound database 110; a converting module 120; a training data store 130; and a training module 140.

The chemical compound database 110 may be a database that stores information about chemical compounds. The chemical compounds registered in the chemical compound database 110 may include various chemical compounds, each of which may be categorized into molecules, ionic compounds, intermetallic compounds and complexes, and may be used in a variety of fields including organic chemistry, inorganic chemistry, biochemistry, pharmacy, etc. The chemical compound database 110 may store a name, an expression describing a chemical structure, and property information for each chemical compound.

The expression may be in a form of SDF (Structured Data Format) that allows for handling the chemical structure of the chemical compound on computer systems. SMILES (Simplified Molecular Input Line Entry System) expression, which is a line notation for describing the chemical structure, is one of most popular human-readable formats. For simplicity, most of the discussion that follows is focused to SMILES as the format of the expression describing the chemical structure; although other expressions such as SMARTS expression may also be used with one or more embodiments of the present invention. Also there are known several types of SMILES. In one or more particular embodiments, any types of SMILES can be used without departing from the scope of the invention. However, in order to ensure uniqueness of molecules in the chemical compound database 110, canonical SMILES that may be a unique expression generated by any known canonicalization algorithms for given a molecule can be used in preferable embodiments.

The expression may be a string including a plurality of concatenating symbols, each of which represents a type of element such as atoms, bonds, etc. The atoms may include non-aromatic atoms (e.g. "B", "C", "N", "O", "P", "S", etc.) and aromatic atoms (e.g. "c", "o", "n", etc.) in the organic subset, and non-organic atoms (e.g. [Au], etc.) in a subset other than the organic subset. The bonds may include single bonds (which are explicitly represented by "—" but typically omitted) and multiple bonds such as double bonds (e.g. "="), triple bonds (e.g. "#"), etc. between adjacent atoms. The other types of the element may include connectivity between non-adjacent atoms such as ring closure, branching (e.g. "(" and ")"), stereochemical configuration for double bonds, tetrahedral centers, etc. (e.g. "/", "¥(backslash)", "@", "@ @").

Note that the expression may describe a whole chemical structure of the chemical compound in some cases, but the expression may describe a partial chemical structure of the chemical compound by using wildcard or dummy atoms in other cases.

The property information may include a value of property such as physical properties including boiling point, melting point, solubility, odor, etc.; chemical properties including reactivity, flammability, toxicity, etc.; and biochemical properties such as pharmacological activity, etc.; to name but a few for each type of the property. Instead of using the values of the property, the property information may include a label or tag for grouping the chemical compounds with a similar property.

The converting module 120 may convert the expression obtained from the chemical compound database 110 into a new expression to generate training data, for each chemical compound in a certain target set. The target set of the chemical compounds may be extracted from the chemical compound database 110 by using a query condition on the property information. For example, chemical compounds with a value of a specific property in a certain range (e.g. a chemical compounds that have boiling points above a specific threshold) may be extracted as target. Alternatively, chemical compounds associated with a specific label or tag may be extracted as target.

In the describing embodiment, the converting module 120 may be configured to read the expression from the chemical compound database 110 for each chemical compound in the target set. The converting module 120 may be configured to enumerate one or more combinations of a position and a type of a structural element appeared in the expression for each chemical compound in the target set. The converting module 120 may be further configured to generate the training data based on the one or more enumerated combinations for each chemical compound in the target set.

Note that the training data may include one or more values with a fixed size. Each value may indicate whether or not a corresponding type of the structural element does appear at a corresponding position for each enumerated combination. Also note that the structural element in the combination may correspond to one or more symbols in the string (i.e., one or more elements in the expression). Thus, types of the structural element may be or may not be identical to the types of the element in the expression.

In the describing embodiment, the converting module 120 may include an augmenting module 122. The augmenting module 122 may be configured to augment the training data by shifting positions of the structural elements and/or by inserting a space between the structural elements to generate one or more additional training data for each chemical compound in the target set. Further details about the augmentation will be described later.

The training data store 130 may store the training data generated by the converting module 120 for each compound in the target set of the chemical compounds. The training data stored in the training data store 130 may include original training data merely converted by the converting module 120 and the one or more additional training data augmented by the augmenting module 122 for each chemical compound in the target set.

The training module 140 may create a neural network 150 and train the neural network 150 based on the training data stored in the training data store 130. The trained neural network 150 would acquire an ability to capture a structural feature specific to the target set of chemical compounds. The neural network to be trained may be a neural network that can accept fixed length of the input, more specifically, a feed forward network generally having fully-connected layers. For simplicity, most of the discussion that follows is focused to the fully connected feed forward neural network (including almost fully connected neural network with partial disconnection); although other architecture of the neural networks may be used with one or more embodiments of the present invention.

As shown in FIG. 1, the chemical structure analyzing system 100 may further include an analyzing module 160. The analyzing module 130 may read parameters of the trained neural network 150 and analyze the trained neural network 150 to extract a structural feature 170. In a describing embodiment, the analyzing module 160 may be configured to extract information related to the structural feature specific to the target set of the chemical compounds by finding one or more input units strongly connected to a predetermined intermediate unit in the trained neural network 150. The analyzing module 130 may output the information about the structural feature 170 specific to the target set of the chemical compounds.

There may be mainly two types of analyses which the chemical structure analyzing system 100 can perform. The first type of the analysis may be analysis that tries to extract a partial structural feature that is considered to contribute a property similarly or commonly observed in chemical compounds in the target set. The second type of the analysis may be analysis that tries to extract a partial structural feature that is considered to discriminate groups of chemical compounds with respective similar properties.

For the first type of the analysis, the target set of the chemical compounds may be designated such that one group of chemical compounds with a similar property are included in the target set. The group may include chemical compounds labeled with same label and/or chemical compounds satisfying a same predetermined condition. For the first type of the analysis, an autoencoder 150A with one or more hidden layers can be employed as the neural network 150. If the autoencoder 150A is employed, the training module 140 may train the autoencoder 150A so as to enable it to reconstruct the training data well.

In a preferable embodiment, the training module 140 may impose a sparsity constraint, which limits number of activation of each hidden unit, on the autoencoder 150A. The autoencoder with the sparsity constrain may be called as a "sparse autoencoder".

For the first type of the analysis, the analyzing module 160 may extract information about the partial structural feature from the autoencoder 150A, which is considered to contribute similar property observed in chemical compounds in the target set.

For the second type of the analysis, the target set of the chemical compounds may be designated such that a plurality of groups, each of which includes chemical compounds with a respective similar property, are included in the target set. Each group may include chemical compounds labeled with respective same label and/or chemical compounds satisfying a respective predetermined condition. The similar property in one group may be different from the similar property in other group.

For the second type of the analysis, a neural network classifier 150B with one or more hidden layers can be employed as the neural network 150. If the neural network classifier 150B is employed, the training module 140 may train the neural network classifier 150B so as to enable it to discriminate the chemical compounds into appropriate groups well. In this case, label information assigned to each group of the chemical compounds may be used as supervised information.

The analyzing module 160 may extract information about the partial structural feature that is considered to discriminate the groups of the chemical compounds with respective similar property.

In the describing embodiment, either of the autoencoder 150A and the neural network classifier 150B, both of which fall into a category of feed forward network, is employed as the neural network 150. However, the aforementioned specific neural network architectures are examples to which the present technique can be applied, but other neural network architectures may be employed in one or more other embodiments according to the present invention.

Also, in the describing embodiment, the trained neural network 150 may be utilized to extract the structural feature specific to the target set of the chemical compounds. However, ways of utilizing the trained neural network 150 may not be limited to the aforementioned way. In one or more other embodiments, the trained neural network 150 can be used as classifier that classifies target chemical compound into known classes. In the other embodiment, the analyzing module 160 may obtain an output or activation from the trained neural network 150 by inputting an input data representing a target chemical compound, which is other than the chemical compounds in the target set used for training.

In particular embodiments, each of modules 110, 120, 122, 130, 140, 150, 160 and 170 described in FIG. 1 may be, but not limited to, implemented as a software module including program instructions and/or data structures in conjunction with hardware components such as a processor, a memory, etc.; as a hardware module including electronic circuitry; or as a combination thereof. These modules 110, 120, 122, 130, 140, 150, 160 and 170 described in FIG. 1 may be implemented on a single computer device such as a personal computer and a server machine or over a plurality of devices such as a computer cluster of the computer devices in a distributed manner.

Figure 2:
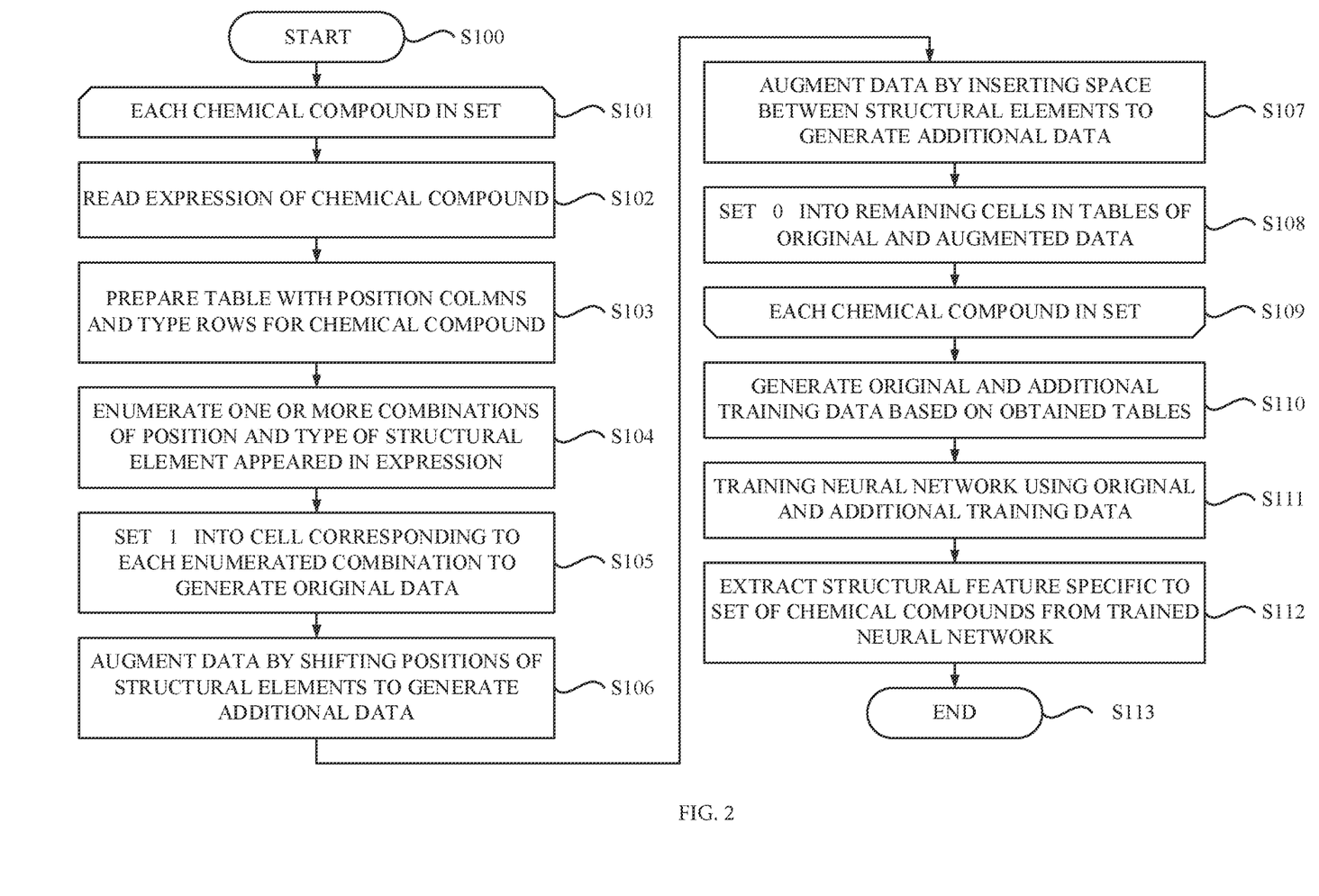
FIG. 2 is a flowchart depicting a process for extracting a structural feature specific to a set of chemical compounds in the chemical structure analyzing system according to the exemplary embodiment of the present invention.

With referring to FIGS. 2-4, a novel process for extracting the structural feature specific to the target set of the chemical compounds will be described. FIG. 2 shows a flowchart depicting the process for extracting the specific structural feature in the chemical structure analyzing system 100 shown in FIG. 1. FIG. 3 and FIG. 4 describe schematics of conversion from a chemical structure into training data and augmentation for each chemical compound of the set in the chemical structure analyzing system 100, respectively.

The process shown in FIG. 2 may begin in response to receiving a request for analysis with arguments that specify the target set of the chemical compounds and the target of the analysis. Note that the process shown in FIG. 2 may be performed by a processing unit that implements the converting module 120, the training module 140 and the analyzing module 160 shown in FIG. 1. A user may request of the processing unit to perform the analysis via command line interface or graphical user interface.

During a loop from step S101 through step S109, the processing unit may perform a novel conversion algorithm by using the converting module 120 for each chemical compounds in the target set.

At step S102, the processing unit may read the expression describing a structure of the chemical compound from the chemical compounds database 110. As shown in FIG. 3, the chemical structure of certain chemical compound (that is allyl cyanide or 3-butenenitrile in the example shown in FIG. 3A) can be expressed as a SMILES expression shown in FIG. 3B. In the SMILES expression, single bonds and hydrogen atoms are omitted. Also if the chemical structure includes a ring, the ring is broken to give a spanning tree structure.

Figure 3A:
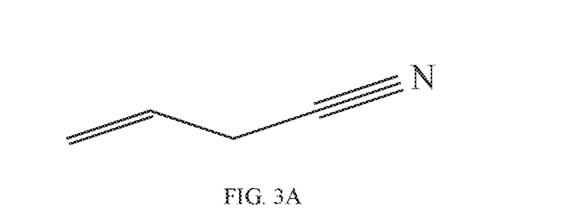
FIG. 3 describes schematics of conversion from a chemical structure into training data in the chemical structure analyzing system according to the exemplary embodiment of the present invention.
Figure 3B:
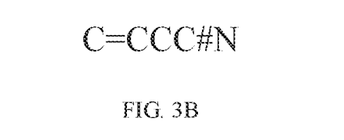
Figure 3C:
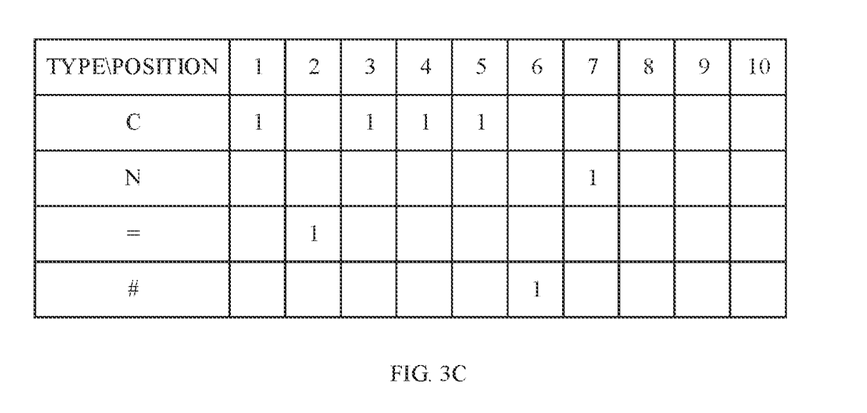

At step S103, the processing unit may prepare a table that has a first axis (columns) and a second axis (rows) exemplary shown in FIG. 3C. Note that values in the table may be filled in later steps.

Figure 3D:
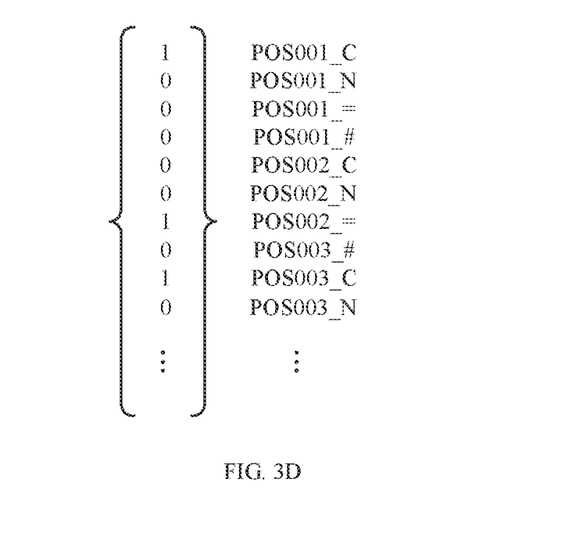

In the table, the first axis (columns) may represent positions of the structural elements in the expression, which is ranging from a start position to end position. The second axis (rows) may represent types of the structural elements. In the example shown in FIG. 3, four structural elements including the carbon atom ("C"), the nitrogen atom ("N"), the double bond ("=") and the triple bond ("#") appear in the SMILES expression and four rows corresponding to the aforementioned four structural elements are created in the table. The end position (consequently width of the table) may be depending on the maximum number of the structural elements in the expression among the target set of the chemical compounds. The end position and the width may be set a value equal to or larger than the maximum number of the structural elements among the target set. In FIG. 3, the end position is set to be ten (10) for simplicity. The values in the table in FIG. 3C can be seen in FIG. 3D. In FIG. 3D, position 1 is represented as "POS001." The structural elements for position 1 are represented as "POS001_C," "POS001_N," "POS001_=," and "POS001_#," with values shown for each of the positions corresponding to each the structural values. For example, the value associated with POS001_C is 1, the value associated with POS001_N is 0, the value associated with POS001_= is 0, etc. This type of representation is repeated for each of the positions. For example, position 2 is represented as POS002, position 3 is represented as POS003, etc.

In the describing embodiment, the types of the structural elements for the second axis may correspond to the elements appeared in the expression in a one-to-one manner. However, in other embodiments, a plurality of the elements appeared in the expression can be represented by a single specific structural element by using an appropriate dictionary, which may be compiled based on physical and/or chemical knowledge about partial structures in the chemical compounds. For examples, specific row for specific partial structure (e.g. aromatic rings) may be added to the table or may replace one or more original rows corresponding to specific partial structure.

Thus, each structural element may represent any one of atoms, bonds, branching, stereochemical configurations and specific partial structures. The atoms may include non-aromatic atoms, aromatic atoms and non-organic atoms. The bonds may include single bonds, double bonds, triple bond, etc. The specific partial structures may include functional groups and other moieties of molecules.

At step S104, the processing unit may enumerate one or more combinations of the position and the type of the structural element appeared in the expression. According to the example shown in FIG. 3B, combinations {(1, "C"), (2, "="), (3, "C"), (4, "C"), (5, "C"), (6, "#"), (7, "N")} can be enumerated at step S104. At step S105, the processing unit may set a first specific value ("1") into a cell designated by each enumerated combination so as to generate the original data for training. As shown in FIG. 3C, the cells corresponding to the enumerated combinations {(1, "C"), (2, "="), (3, "C"), (4, "C"), (5, "C"), (6, "#"), (7, "N")} may be set with the first specific value ("1"). Each first specific value in the table indicates that a corresponding type of the structural element does appear at a corresponding position in the expression.

At step S106, the processing unit may augment the data by horizontally shifting positions of the structural elements appeared in the expression to generate one or more additional data for training.

Figure 4A:
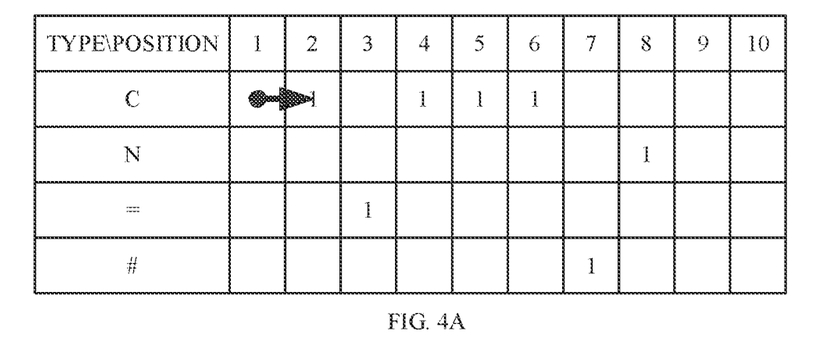
FIG. 4 describes schematics of augmentation for each chemical compound of the set in the chemical structure analyzing system according to the exemplary embodiment of the present invention.
Figure 4B:
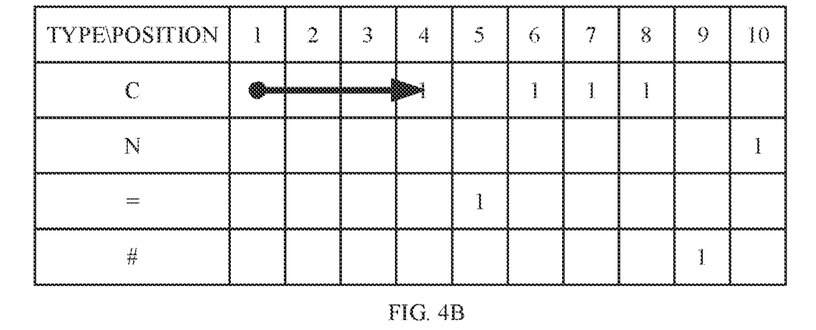

FIGS. 4A and 4B show examples of the augmentation by the horizontal shift. In an example shown in FIG. 4A, each position of each enumerated combination is shifted to left horizontally by one. In other example shown in FIG. 4B, each position of each enumerated combination may be shifted to left by two from the original position. In a particular embodiment, the augmentation may be done by randomly performing a predetermined number of possible shifting operations. In other particular embodiment, the augmentation may be done by exhaustively performing all possible shifting operations.

At step S107, the processing unit may augment the data by inserting one or more spaces between the structural elements connected via a specific structural element in the expression so as to generate one or more additional data for training. The specific structural elements can be designated by using an appropriate dictionary that may be compiled based on physical and/or chemical knowledge about chemical bond. The specific structural element may be a single bond that does not participate in the aromaticity (e.g., single bond between non aromatic carbon atoms).

Figure 4C:
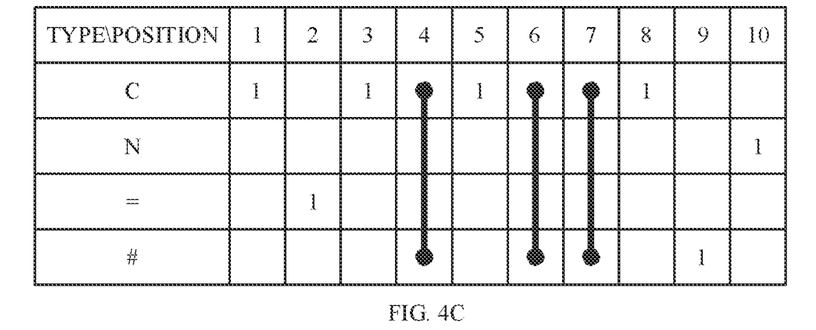
Figure 4D:
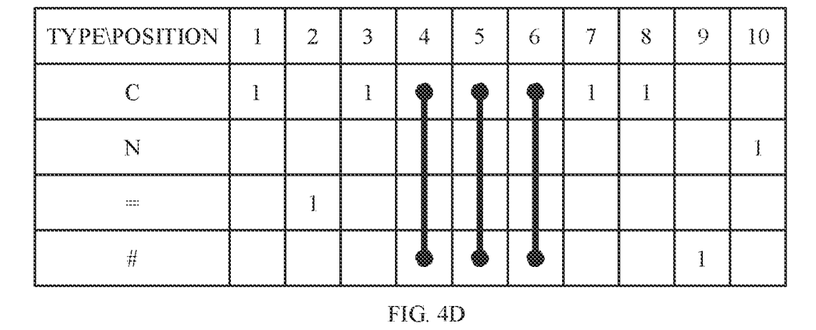

FIGS. 4C and 4D show examples of the augmentation by the space insertion. In an example shown in FIG. 4C, one space and two spaces are inserted between two pairs of the non-aromatic carbon atoms connected via the single bond, respectively. In other example shown in FIG. 4D, three spaces are inserted between one of the two pairs of the non-aromatic carbon atoms connected via the single bond. In a particular embodiment, the augmentation may be done by randomly performing a predetermined number of possible inserting operations. In other particular embodiment, the augmentation may be done by exhaustively performing all possible inserting operations.

Also, the examples shown in FIGS. 4C and 4D, the space insertion may be done based on an original position in the original data. However, in a particular embodiment, one or more spaces may be inserted into the additional data that is generated by shifting the original position of the original data at step 106.

At step S108, the processing unit may set a second specific value ("0") into remaining cells in the tables of the original and additional data. Each second specific value in the table may indicate that the corresponding type of the structural element does not appear at the corresponding position in the expression.

When the loop from step S101 through step S109 has executed for all chemical compounds in the target set, the process proceeds to step S110.

At step S110, the processing unit may generate original and additional training data by the converting module 120 based on obtained tables of the original and additional data. Each table may include the one or more combinations enumerated at the step S104 for each chemical compound in the target set. Each training data may be in a form of bag-of-words type vector including one or more entries with the fixed size. Each entry may correspond to each combination in the whole combinations that may be totally enumerated for the target set of the chemical compounds. Each entry may holds the first specific value ("1") or the second specific value ("0"), which indicates whether or not the corresponding type of the structural element does appear at the corresponding position for each combination.

At step S111, the processing unit may train the neural network 150 by the training module 140 based on the original and additional training data that is obtained for the target set of the chemical compounds. Parameters of the neural network 150, which may include weights between each units and biases of each unit, are optimized by appropriate training algorithm.

If the autoencoder 150A is used, the processing unit may train the autoencoder 150A in unsupervised manner so as to enable it to reconstruct the training data well. If the neural network classifier 150B is used, the processing unit may train the neural network classifier 150B in a supervised manner by using the label information assigned to each group of the chemical compounds so as to enable it to discriminate the chemical compounds into appropriate groups well.

At step S112, the processing unit may extract information related to the structural feature specific to the target set of the chemical compounds from the trained neural network 150. As described above, the trained neural network 150 can acquire an ability to capture the structural feature specific to the target set. By analyzing parameters of the trained neural network 150, one or more specific input units, each of which has at least one connection to any of one or more predetermined intermediate units stronger than other input units, can be found. The one or more input units may represent a continuous structure or distant structures.

The predetermined intermediate unit may be any one of the intermediate hidden units included in the neural network 150. In an embodiment, the one or more predetermined intermediate units used for analyzing may be designated by a user or given as a default for the neural network 150 used.

For example, if the neural network 150 has merely one hidden layer, the one or more predetermined intermediate hidden units used for analyzing may be hidden units in the hidden layer. Strongest k-connections for each intermediate hidden unit can be enumerated and the one or more input units involved in any of the enumerated connections can be simply extracted as the information describing the specific structural feature. If the neural network 150 has two or more hidden layers, the one or more predetermined intermediate hidden units used for analyzing may be hidden units in a bottleneck layer that has narrowest width. The one or more input units connected to any of the one or more predetermined intermediate hidden units through connections with stronger weight can be extracted as the information describing the specific structural feature.

In particular embodiment, the vector expression of the training data can indicate not only presence of structural element but also positional relation between the structural elements in the expression; the vector expression of the training data and the expression in the form of human readable format can be reversibly converted each other; thereby the vector expression based on the extracted input units can tell us information about the partial structural feature specific to the target set of the chemical compounds.

In the preferable embodiments employing the feed forward neural network that does not have any subsampling layer (it can be seen in CNNs) and any connections forming a directed cycle (it can be seen in RNNs), a downstream input unit corresponding to upstream activated hidden unit can be easily found by reversely traversing strong connections from the upstream activated hidden unit.

Also, in the preferable embodiments involving the augmentation of the training data, the specific partial structural feature can be extracted robustly with respect to absolute position in the expression even though the feed forward neural network are utilized.

Note that some embodiments may not have these potential advantages and these potential advantages are not necessarily required of all embodiments.

Experimental Studies

A program implementing the system shown in FIG. 1 and the process shown in FIG. 2 according to the exemplary embodiment was coded and executed for given set of 180 chemical compounds. An autoencoder that has an input layer of 1530 units, a bottleneck layer of 100 hidden units and an output layer of 1530 units was created. The table width was set be 70 that was larger than the maximum length of the SMILES expression among the compounds in the given set. The original and additional training data for each chemical compound in the given set were prepared by the novel conversion algorithm. The additional data was generated by the augmentation up to ten for each chemical compound in the given set. The created autoencoder was trained by using the prepared original and additional training data.

As an example, strongest three (3) connections for each hidden unit in the trained autoencoder were enumerated. Continuous structures corresponding to the input units involved in any of the enumerated connections were extracted as the specific structural feature. The structures such as "ccc", "CCC" and "Br" were observed as the structural feature specific the target set of the chemical compounds.

Computer Hardware Component

Figure 5:
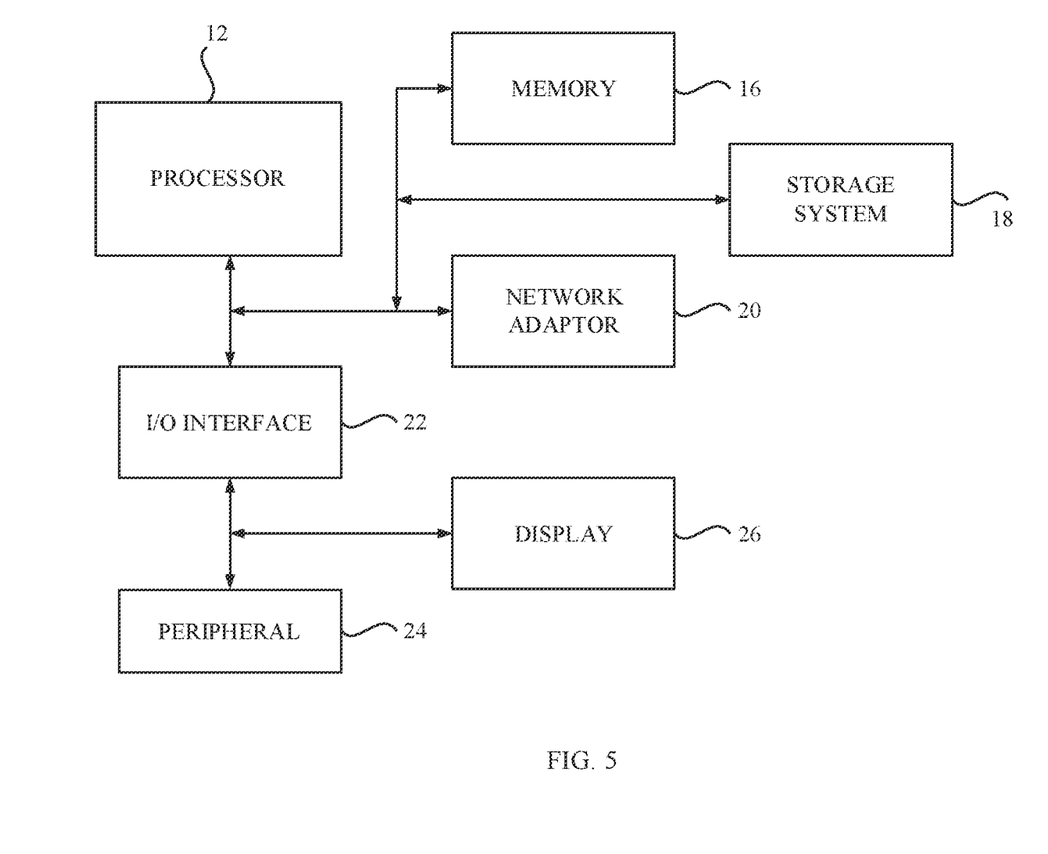
FIG. 5 depicts a computer system according to one or more embodiment of the present invention.

Referring now to FIG. 5, a schematic of an example of a computer system 10, which can be used for the chemical structure analyzing system 100, is shown. The computer system 10 shown in FIG. 5 is implemented as computer system. The computer system 10 is only one example of a suitable processing device and is not intended to suggest any limitation as to the scope of use or functionality of embodiments of the invention described herein. Regardless, the computer system 10 is capable of being implemented and/or performing any of the functionality set forth hereinabove.

The computer system 10 is operational with numerous other general purpose or special purpose computing system environments or configurations. Examples of well-known computing systems, environments, and/or configurations that may be suitable for use with the computer system 10 include, but are not limited to, personal computer systems, server computer systems, thin clients, thick clients, handheld or laptop devices, in-vehicle devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system 10 may be described in the general context of computer system-executable instructions, such as program modules, being executed by a computer system. Generally, program modules may include routines, programs, objects, components, logic, data structures, and so on that perform particular tasks or implement particular abstract data types.

As shown in FIG. 5, the computer system 10 is shown in the form of a general-purpose computing device. The components of the computer system 10 may include, but are not limited to, a processor (or processing unit) 12 and a memory 16 coupled to the processor 12 by a bus including a memory bus or memory controller, and a processor or local bus using any of a variety of bus architectures.

The computer system 10 typically includes a variety of computer system readable media. Such media may be any available media that is accessible by the computer system 10, and it includes both volatile and non-volatile media, removable and non-removable media.

The memory 16 can include computer system readable media in the form of volatile memory, such as random access memory (RAM). The computer system 10 may further include other removable/non-removable, volatile/non-volatile computer system storage media. By way of example only, the storage system 18 can be provided for reading from and writing to a non-removable, non-volatile magnetic media. As will be further depicted and described below, the storage system 18 may include at least one program product having a set (e.g., at least one) of program modules that are configured to carry out the functions of embodiments of the invention.

Program/utility, having a set (at least one) of program modules, may be stored in the storage system 18 by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of embodiments of the invention as described herein.

The computer system 10 may also communicate with one or more peripherals 24 such as a keyboard, a pointing device, a car navigation system, a audio system, etc.; a display; one or more devices that enable a user to interact with the computer system 10; and/or any devices (e.g., network card, modem, etc.) that enable the computer system 10 to communicate with one or more other computing devices. Such communication can occur via Input/Output (I/O) interfaces 22. Still yet, the computer system 10 can communicate with one or more networks such as a local area network (LAN), a general wide area network (WAN), and/or a public network (e.g., the Internet) via the network adapter 20. As depicted, the network adapter 20 communicates with the other components of the computer system 10 via bus. It should be understood that although not shown, other hardware and/or software components could be used in conjunction with the computer system 10. Examples, include, but are not limited to: microcode, device drivers, redundant processing units, external disk drive arrays, RAID systems, tape drives, and data archival storage systems, etc.

Computer Program Implementation

The present invention may be a computer system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more aspects of the present invention has been presented for purposes of illustration and description, but is not intended to be exhaustive or limited to the invention in the form disclosed.

Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A computer implemented method for training a neural network to capture a structural feature specific to a set of chemical compounds, the method comprising:
    reading an expression describing a structure of each chemical compound in the set of chemical compounds, the expression comprising a string including a plurality of concatenating symbols;
    enumerating one or more combinations of a position and a type of a structural element appearing in the expression describing the structure of each chemical compound in the set of chemical compounds;
    generating training data based on the one or more enumerated combinations for each chemical compound in the set of chemical compounds and extracted property information, the training data including one or more values having a size, and indicating whether or not a corresponding type of the structural element appears at a corresponding position for each combination;
    augmenting the training data by executing a predetermined number of possible shifting operations of one or more positions of the one or more enumerated combinations, the shifting including inserting a space between structural elements connected via a specific element in the expression for the chemical compound to generate one or more additional training data; and
    training the neural network based on the training data for the set of the chemical compounds.

2. The method of claim 1, wherein the method further comprises:
    extracting information related to a structural feature specific to the set of the chemical compounds by finding one or more input units connected to a predetermined intermediate unit in the neural network.

3. The method of claim 2, wherein the set includes a group of chemical compounds having a similar property and the training includes training the neural network so as to enable the neural network to reconstruct the training data, the structural feature being a partial structural feature considered to contribute the similar property.

4. The method of claim 2, wherein the set includes a first group of first chemical compounds having a first similar property and a second group of second chemical compounds having a second similar property, and the training includes training the neural network so as to enable the neural network to discriminate the chemical compounds into the first and second groups, the structural feature being a partial structural feature considered to discriminate between the first and second chemical, compounds.

5. The method of claim 2, wherein the extracting includes:
    analyzing parameters in the trained neural network to find the one or more input units each having a connection to the predetermined intermediate unit stronger than other input units, the one or more input units representing a continuous structure or distant structures.

6. The method of claim 1, wherein the method further comprises:
    preparing a table having a first axis and a second axis for each chemical compound in the set, the first axis representing positions ranging from a start position to an end position depending on a maximum number of the structural elements among the set of the chemical compounds, and the second axis representing types of the structural elements;
    setting a first value into a cell designated by each combination of the one or more enumerated combinations, for each chemical compound in the set; and
    setting a second value into remaining cells, for each chemical compound in the set.

7. The method of claim 1, wherein the augmenting the training data further comprises shifting positions of the structural elements appearing in the expression for the chemical compound to generate the one or more additional training data.

8. The method of claim 1, wherein the augmenting the training data further comprises inserting a plurality of spaces between the structural elements connected via a specific element in the expression for the chemical compound to generate the one or more additional training data.

9. The method of claim 1, wherein the expression is in a form of human-readable format and the neural network is a neural network that accepts a fixed length input.

10. The method of claim 1, wherein the expression is a string in a form of SMILES expression, the structural element corresponds to one or more symbols in the string, and the neural network is a feed forward neural network.

11. The method of claim 1, wherein each of the structural elements represents an atom, a bond, a branching, a stereochemical configuration, and a partial chemical structure.

12. A computer system for training a neural network to capture a structural feature specific to a set of chemical compounds, by executing program instructions, the computer system comprising:
    a memory tangibly storing the program instructions; and
    a processor in communications with the memory, wherein the computer system is configured to
        read an expression describing a structure of each chemical compound in the set of chemical compounds, the expression comprising a string including a plurality of concatenating symbols;
        enumerate one or more combinations of a position and a type of a structural element appearing in the expression describing the structure of each chemical compound in the set of chemical compounds;
        generate training data based on the one or more enumerated combinations for each chemical compound in the set of chemical compounds and extracted property information, the training data including one or more values having a size, and indicating whether or not a corresponding type of the structural element appears at a corresponding position for each combination;

augment the training data by executing a predetermined number of possible shifting operations of one or more positions of the one or more enumerated combinations, the shifting including inserting a space between structural elements connected via a specific element in the expression for the chemical compound to generate one or more additional training data; and train the neural network based on the training data for the set of the chemical compounds.

13. The computer system of claim 12, wherein the computer system is further configured to:

extract information related to a structural feature specific to the set of the chemical compounds by finding one or more input units connected to a predetermined intermediate unit in the neural network.

14. The computer system of claim 12, wherein the computer system is further configured to:

prepare a table having a first axis and a second axis for each chemical compound in the set, the first axis representing positions ranging from a start position to end position depending on a maximum number of the structural elements among the set of the chemical compounds, and the second axis representing types of the structural element;

set a first value into a cell designated by each combination of the one or more enumerated combinations-, for each chemical compound in the set; and set a second value into remaining cells, for each chemical compound in the set.

15. The computer system of claim 12, wherein the computer system is further configured to:

further augment the training data by shifting positions of the structural elements appearing in the expression for the chemical compound to generate the one or more additional training data.

16. The computer system of claim 12, wherein the computer system is further configured to:

further augment the training data by inserting a plurality of spaces between the structural elements connected via a specific element in the expression for the chemical compound to generate the one or more additional training data.

17. A computer program product for training a neural network to capture a structural feature specific to a set of chemical compounds, the computer program product comprising a non-transitory computer readable storage medium having program instructions embodied therewith, the program instructions executable by a computer to cause the computer to perform a method comprising:

reading an expression describing a structure of each chemical compound in the set of chemical compounds, the expression comprising a string including a plurality of concatenating symbols;

enumerating one or more combinations of a position and a type of a structural element appearing in the expression describing the structure of each chemical compound in the set of chemical compounds;

generating training data based on the one or more enumerated combinations for each chemical compound in the set of chemical compounds and extracted property information, the training data including one or more values having a size, and indicating whether or not a corresponding type of the structural element appears at a corresponding position for each combination;

augmenting the training data by executing a predetermined number of possible shifting operations of one or more positions of the one or more enumerated combinations, the shifting including inserting a space between structural elements connected via a specific element in the expression for the chemical compound to generate one or more additional training data; and training the neural network based on the training data for the set of the chemical compounds.

18. The computer program product of claim 17, wherein the method further comprises:

extracting information related to a structural feature specific to the set of the chemical compounds by finding one or more input units connected to a predetermined intermediate unit in the neural network.

19. The computer program product of claim 17, wherein the method further comprises:

preparing a table having a first axis and a second axis for each chemical compound in the set, the first axis representing positions ranging from a start position to end position depending on a maximum number of the structural elements among the set of the chemical compounds, and the second axis representing types of the structural elements;

setting a first value into a cell designated by each combination of the one or more enumerated combinations, for each chemical compound in the set; and setting a second value into remaining cells, for each chemical compound in the set.

20. The computer program product of claim 17, wherein the augmenting the training data further comprises shifting positions of the structural elements appearing in the expression for the chemical compound to generate the one or more additional training data.

* * * * *